United States Patent [19]

Frickel et al.

[11] 4,168,317

[45] Sep. 18, 1979

[54] AMINO DERIVATIVES OF 4-HYDROXY-1,2-BENZISOTHIAZOLE

[75] Inventors: Fritz-Frieder Frickel, Ludwigshafen; Helmut Hagen, Frankenthal; Ulrich Ohnsorge, Goennheim; Albrecht Franke, Wachenheim; Dieter Lenke, Ludwigshafen; Josef Gries, Wachenheim; Hans D. Lehmann, Hirschberg-Leutershausen, all of Fed. Rep. of Germany

[73] Assignee: BASF Aktiengesellschaft, Fed. Rep. of Germany

[21] Appl. No.: 873,546

[22] Filed: Jan. 30, 1978

[30] Foreign Application Priority Data

Feb. 5, 1977 [DE] Fed. Rep. of Germany ....... 2704794

[51] Int. Cl.$^2$ ..................... A61K 31/38; C07D 275/04
[52] U.S. Cl. .................................... 424/275; 548/207; 546/198; 260/245.5
[58] Field of Search .................... 260/304 A; 424/275

[56] References Cited

U.S. PATENT DOCUMENTS 3,997,548  12/1976  Sengemann ...................... 260/304 A

FOREIGN PATENT DOCUMENTS 1058822  2/1967  United Kingdom ................ 260/288 R

OTHER PUBLICATIONS

Justies Liebigs Annalen des Organishe Chemie, Band 27, p. 280.
Morris, William-editor, The American Heritage Dictionary, Houghton Mifflin Co., Boston, 1976, p. 1049.

Primary Examiner—Donald G. Daus
Assistant Examiner—Lisa Jones
Attorney, Agent, or Firm—Keil & Witherspoon

[57] ABSTRACT

New aminopropanol derivatives of 4-hydroxy-1,2-benzisothiazole and their addition salts with acids, their preparation, and pharmaceutical formulations which contain the said compounds and may be used for the treatment and prophylaxis of cardiac and circulatory disorders.

10 Claims, No Drawings

AMINO DERIVATIVES OF 4-HYDROXY-1,2-BENZISOTHIAZOLE

The present invention relates to new aminopropanol derivatives of 4-hydroxy-1,2-benzisothiazole and their addition salts with acids, their preparation, and pharmaceutical formulations which contain the said compounds and may be used for the treatment and prophylaxis of cardiac and circulators disorders.

We have found that compounds of the general formula (I)

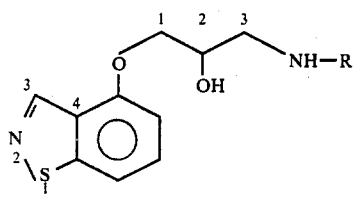

where R is hydrogen or alkyl of 1 to 8 carbon atoms which may be unsubstituted or substituted by hydroxyl, alkoxy of 1 to 3 carbon atoms, alkylthio of 1 to 3 carbon atoms, dialkylamino (where alkyl is of 1 to 5 carbon atoms), cycloalkylamino of 3 to 7 carbon atoms in the ring, cyclic amine of 5 to 7 ring members or cycloalkyl of 3 to 8 carbon atoms in the ring, or is alkenyl or alkynyl of 2 to 8 carbon atoms, or is cycloalkyl or cycloalkenyl of 3 to 8 carbon atoms in the ring or bicycloalkyl of 5 to 8 carbon atoms, the cycloalkyl rings being unsubstituted or monosubstituted or disubstituted by lower alkyl of 1 to 3 carbon atoms, and their addition salts with acids, exhibit valuable pharmacological properties.

Examples of straight-chain or branched alkyl of 1 to 8 carbon atoms are methyl, ethyl, propyl, isopropyl, n-butyl, iso-butyl, sec.-butyl, tert.-butyl, pentyl-2, 2-methyl-butyl-2, 3-methyl-butyl-2, 3-methyl-pentyl-3, 2,3-dimethyl-butyl-2, 3-ethyl-pentyl-3, 2,4-dimethyl-pentyl-3 and 2,4,4-trimethylpentyl, and examples of substituted alkyl are 1-methylthio-2-methyl-propyl-2, 1-methoxy-propyl-2, 2-hydroxy-ethyl-1, 1-hydroxy-butyl-2, 3-hydroxy-3-methyl-butyl-1, 3-piperidinopropyl-2 and 1-cyclopropyl-ethyl-1.

Amongst the alkyl radicals, those of 3 to 6 carbon atoms which are branched at the carbon in the α-position to the amino nitrogen are preferred. Thus, preferred alkyl radicals are isopropyl, tert.-butyl, 2-methyl-butyl-2, sec.-butyl, 3-methylpentyl-3 and pentyl-2. Suitable substituents of the preferred alkyl radicals are, in particular, alkoxy of 1 to 3 carbon atoms and especially methoxy, so that an example of a preferred substituted alkyl is 1-methoxy-propyl-2.

Examples of alkenyl or alkynyl of 2 to 8 carbon atoms are prop-1-enyl-3, but-3-ynyl-2, 2-methyl-but-3-ynyl-2 and 3-ethylpent-1-ynyl-3. Amongst these, alkynyl radicals of 3 to 6 carbon atoms, e.g. but-3-ynyl-2 and 2-methyl-but-3-ynyl-2, are preferred.

Examples of cycloalkyl, cycloalkenyl and bicycloalkyl are cyclopropyl, cyclobutyl, cyclopentyl, cycloheptyl, bicyclo[3.3.0]-octyl, 3-exo-norbornanyl, cyclooctenyl-5 and dimethylcyclohexyl, a suitable alkyl substituent of the said cyclic radicals being, in particular, methyl.

Accordingly, examples of compounds according to the invention, of the formula I, are: 4-(2-hydroxy-3-tert.-butylamino-propoxy)-1,2-benzisothiazole, 4-[2-hydroxy-3-(3-methylbutyl-2-amino)-propoxy]-1,2-benzisothiazole, 4-(2-hydroxy-3-amino-propoxy)-1,2-benzisothiazole, 4-(2-hydroxy-3-methylaminopropoxy)-1,2-benzisothiazole, 4-(2-hydroxy-3-n-butylaminopropoxy)-1,2-benzisothiazole, 4-(2-hydroxy-3-isobutylaminopropoxy)-1,2-benzisothiazole, 4-(2-hydroxy-3-sec.-butylaminopropoxy)-1,2-benzisothiazole, 4-[2-hydroxy-3-(2-methyl-butyl-2-amino)-propoxy]-1,2-benzisothiazole, 4-[2-hydroxy-3-(3-methyl-pentyl-3-amino)-propoxy]-1,2-benzisothiazole, 4-[2-hydroxy-3-(2,3-dimethyl-butyl-2-amino)-propoxy]-1,2-benzisothiazole, 4-[2-hydroxy-3-(3-ethyl-pentyl-3-amino)-propoxy]-1,2-benzisothiazole, 4-[2-hydroxy-3-(2,4-dimethyl-pentyl-3-amino)-propoxy]-1,2-benzisothiazole, 4-(2-hydroxy-3-cyclopropylamino-propoxy)-1,2-benzisothiazole, 4-(2-hydroxy-3-cyclopentylamino-propoxy)-1,2-benzisothiazole, 4-(2-hydroxy-3-cycloheptylamino-propoxy)-1,2-benzisothiazole, 4-[2-hydroxy-3-(bicyclo[3.3.0]-octyl-1-amino)-propoxy]-1,2-benzisothiazole, 4-[2-hydroxy-3-(2-exo-norbornanylamino)-propoxy]-1,2-benzisothiazole, 4-[2-hydroxy-3-(2,4,4-trimethyl-pentyl-2-amino)-propoxy]-1,2-benzisothiazole, 4-[2-hydroxy-3-(1-thiomethyl-2-methyl-propyl-2-amino)-propoxy]-1,2-benzisothiazole, 4-[2-hydroxy-3-(2-methyl-but-3-ynyl-2-amino)-propoxy]-1,2-benzisothiazole, 4-[2-hydroxy-3-(but-3-ynyl-2-amino)-propoxy]-1,2-benzisothiazole, 4-[2-hydroxy-3-(1-methoxy-propyl-2-amino)-propoxy]-1,2-benzisothiazole, 4-[2-hydroxy-3-(cyclooctenyl-5-amino)-propoxy]-1,2-benzisothiazole, 4-[2-hydroxy-3-(2,6-dimethyl-cyclohexyl-1-amino)-propoxy]-1,2-benzisothiazole, 4[-2-hydroxy-3-(3-ethylpent-1-ynyl-3-amino)-propoxy]-1,2-benzisothiazole, 4-[2-hydroxy-3-(prop-1-enyl-3-amino)-propoxy]-1,2-benzisothiazole, 4-[2-hydroxy-3-(pentyl-2-amino)-propoxy]-1,2-benzisothiazole, 4-[2-hydroxy-3-(1-cyclopropyl-ethyl-1-amino)-propoxy]-1,2-benzisothiazole, 4-[2-hydroxy-3-(2-hydroxy-ethylamino)-propoxy]-1,2-benzisothiazole, 4-[2-hydroxy-3-(1-hydroxy-butyl-2-amino)-propoxy]-1,2-benzisothiazole and 4-[2-hydroxy-3-(3-cyclohexyl-amino-propyl-2-amino)-propoxy]-1,2-benzisothiazole.

Further examples are 4-[2-hydroxy-3-(2-cyclobutyl-ethyl-2-amino)-propoxy]-1,2-benzisothiazole, 4-[2-hydroxy-3-(1-cyclopropyl-propyl-1-amino)-propoxy]-1,2-benzisothiazole, 4-(2-hydroxy-3-cyclobutylamino-propoxy)-1,2-benzisothiazole and 4-[2-hydroxy-3-(prop-2-ynyl-1-amino)-propoxy]-1,2-benzisothiazole.

The compounds according to the invention can be manufactured by reacting a 1,2-benzisothiazole of the general formula II

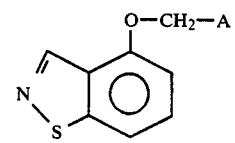

where A is

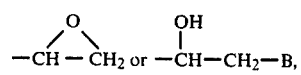

B being a nucleofugic leaving group, with an amine of the general formula

H$_2$N-R where R has the above meanings, advantageously in a solvent, and in the presence or absence of an acid-binding agent, in the conventional manner, with or without conversion of the resulting compound into the addition salt with a physiologically safe acid.

The leaving group B is preferably a halogen, especially chlorine, bromine or iodine. Examples of other nucleofugic leaving groups are aromatic or aliphatic sulfonic acid radicals, e.g. the p-toluenesulfonic acid radical, the p-bromosulfonic acid radical or the methanesulfonic acid radical.

The reactions are carried out at from 10° to 120° C., i.e. at room temperature or elevated temperatures, advantageously at from 50° to 120° C. They may be carried out under atmospheric pressure or in a closed vessel under superatmospheric pressure, with or without heating to a temperature within the stated range. In the case of volatile amines $H_2N$-R, in particular, it may be advantageous to carry out the reaction in a closed system, i.e. in an autoclave.

The starting compounds may be reacted with one another directly, i.e. without adding a diluent or solvent. However, the reactions are advantageously carried out in the presence of an inert diluent or solvent, for example a lower alcohol of 1 to 4 carbon atoms, e.g. methanol, ethanol, n- or isopropanol, preferably isopropanol or ethanol, a lower saturated dialkyl ether, dialkyl glycol ether or cyclic ether, e.g. diethyl ether, 1,2-dimethoxyethane, tetrahydrofuran or dioxane, benzene or an alkylbenzene, e.g. toluene or xylene, an aliphatic hydrocarbon, e.g. hexane, heptane or octane, a lower aliphatic ketone, e.g. acetone, methyl ethyl ketone or methyl isobutyl ketone, a dialkylformamide or diethyl formamide, or dimethylsulfoxide, or in the presence of water, or in mixtures of the above solvents.

The amine of the formula $H_2N$-R used in excess may also serve as a diluent or solvent.

The preferred solvent for the reaction of 1-(1,2-benzisothiazol-4-yloxy)-2,3-epoxypropane with an amine R-$NH_2$ is a lower alcohol, especially ethanol or isopropanol, the reaction preferably being carried out at from 50° C. to 120° C. and under atmospheric pressure.

In the case of the nucleophilic replacement of a radical B, the preferred solvent is a lower aliphatic ketone, e.g. acetone, methyl ethyl ketone or methyl isobutyl ketone, a cyclic ether, especially tetrahydrofuran or dioxane, or a dialkylformamide, e.g. dimethylformamide, and the preferred temperature is from 90° to 120° C.

The reaction may or may not be carried out in the presence of a catalytic amount of sodium iodide or potassium iodide.

It should be mentioned that a mixture of the epoxide with a halohydrin may also be used as the starting compound of the formula II, since the industrial manufacture of the starting compounds of the formula II at times results in such mixtures.

In an advantageous embodiment of the nucleophilic replacement of the radical B by the amine used, the reaction is carried out in the presence of a base as an acid-binding agent. Preferred bases are alkali metal hydroxides, carbonates, bicarbonates and alcoholates, and tertiary organic amines, e.g. pyridine or a trialkylamine, e.g. trimethylamine or triethylamine. Amongst the alkali metal compounds, those of sodium and potassium are particularly suitable. The base is used in the stoichiometric amount or in slight excess. It may also be advantageous to use an excess of the amine $H_2N$-R employed for the reaction to serve, at the same time, as the acid-binding agent.

The time required for complete reaction depends on the reaction temperature and is in general from 2 to 15 hours. The product can be isolated in the conventional manner, for example by filtration, or by distilling the diluent or solvent from the reaction mixture. The compound obtained is purified in the conventional manner, for example by recrystallization from a solvent, by conversion to an adduct with an acid, or by column chromatography.

The starting compounds of the formula (II) can be obtained by alkylating 4-hydroxy-1,2-benzisothiazole, which may be obtained from the known compound 4-methoxy-1,2-benzisothiazole by an ether cleavage reaction, with an epihalohydrin or an $\alpha,\omega$-dihalo-2-propanol.

Suitable epihalohydrins are epichlorohydrin, epibromohydrin and epiiodohydrin, and suitable $\alpha,\omega$-dihalo-2-propanols are, in particular, 1,3-dichloro-2-propanol and 1,3-dibromo-2-propanol.

The reaction of 4-hydroxy-1,2-benzisothiazole in order to prepare the starting compounds of the formula II is advantageously carried out at from 50° to 120° C. under atmospheric pressure or in a closed vessel under superatmospheric pressure. Advantageously, the reaction is carried out in an inert diluent or solvent, for example a lower aliphatic ketone, e.g. acetone, methyl ethyl ketone or methyl isobutyl ketone, a lower alcohol of 1 to 4 carbon atoms, e.g. methanol, ethanol, propanol or butanol, a lower alkyl acetate, e.g. methyl acetate, ethyl acetate or propyl acetate, a dialkylformamide, e.g. dimethylformamide or diethylformamide, or dimethylsulfoxide, or with an excess of the alkylating agent as the diluent or solvent.

The reactions are preferably carried out in the presence of a base as the acid-binding agent. Suitable bases are alkali metal carbonates, bicarbonates, hydroxides and alcoholates, especially of sodium and potassium, basic oxides, e.g. aluminum oxide or calcium oxide, and organic tertiary bases, e.g. pyridine, piperidine or lower trialkylamines, e.g. trimethylamine or triethylamine. In relation to the alkylating agent employed, the bases may be used in catalytic amount or stoichiometric amount or in slight excess.

Preferably, 4-hydroxy-1,2-benzisothiazole is reacted with epibromohydrin or with 1,2-dibromo-2-propanol in a lower aliphatic ketone, especially acetone or methyl isobutyl ketone, in the presence of at least one mole equivalent, based on the alkylating agent, of a base, especially potassium carbonate, at from 50° to 80° C.

Similarly to the process for reacting phenol with 1,3-dichloro-2-propanol, described in Liebigs Annalen der Chemie 1976, 221–224, 4-hydroxy-1,2-benzisothiazole may be reacted with the equivalent amount of 1,3-dichloro-2-propanol in aqueous sodium hydroxide solution at about 50° C.

It should also be mentioned that the starting compounds of the formula II may be interconverted by a simple acid-base reaction. For example, 1-(1,2-benzisothiazol-4-yloxy)-2,3-epoxypropane may be converted to 1-(1,2-benzisothiazol-4-yloxy)-3-halo-propan-2-ol, by means of the appropriate hydrohalic acid, the diluent or solvent used being a conventional solvent for such a reaction or, preferably, an aliphatic or cyclic ether, e.g. diethyl ether, tetrahydrofuran or dioxane, or a lower alcohol, e.g. methanol, ethanol or propanol. Conversely, the 1-(1,2-benzisothiazol-4-yloxy)-3-halo-propan-2-ol compounds, especially 1-(1,2-benzisothiazol-4-yloxy)-3-chloropropan-2-ol and 1-(1,2-benzisothiazol-4-yloxy)-3-bromo-propan-2-ol may be converted by means of a base, e.g. an alkali metal hydroxide, carbonate, bicarbonate, alcoholate or hydride, or an organic amine, e.g. pyridine, piperidine or a tertiary aliphatic amine, e.g. trimethylamine or triethylamine, into 1-(1,2-benzisothiazol-4-yloxy)-2,3-epoxypropane. These reactions may be carried out at room temperature or be accelerated or completed by heating, for example at from 60° to 120° C. The reaction may be carried out under atmospheric pressure or in a closed vessel under superatmospheric pressure, with or without heating. The starting compounds for this reaction may be isolated beforehand or be produced in situ and be directly converted further, without isolation and purification.

According to an alternative process of manufacture, the compounds of the general formula (I) are obtained by alkylating 4-hydroxy-1,2-benzisothiazole with a compound of the general formula III or IV

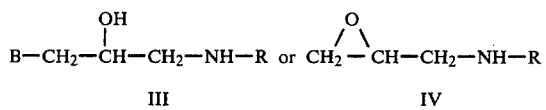

where B and R have the above meanings and preferred meanings, advantageously in a solvent, and in the presence or absence of an acid-binding agent, at from 40° to 120° C., in the conventional manner, and the resulting compound may or may not be converted to its addition salt with a physiologically safe acid.

This reaction may for example be carried out under conditions similar to those described in Swiss Patent 451,115 or in German Laid-Open Application DOS 2,007,751.

The alkylation of 4-hydroxy-1,2-benzisothiazole with a compound of the formula III is preferably carried out in the presence of an acid-binding agent, e.g. an alkali metal hydroxide, carbonate, bicarbonate or alcoholate, or of a tertiary organic amine, preferably pyridine or a tertiary aliphatic amine, e.g. trimethylamine or triethylamine. Amongst the alkali metal compounds, those of sodium and potassium are particularly suitable. The base is advantageously used in the stoichiometric amount or in a slight excess. Equally, the hydroxy-benzisothiazole may, for example, be employed in the form of an alkali metal salt, e.g. the sodium salt or potassium salt.

The alkylation reactions are advantageously carried out in an inert diluent or solvent, for example a lower aliphatic alcohol of 1 to 4 carbon atoms, e.g. methanol, ethanol, propanol, isopropanol or a butanol, or a lower aliphatic ketone, e.g. acetone, methyl ethyl ketone or methyl isobutyl ketone, a cyclic ether, e.g. tetrahydrofuran or dioxane, or a dialkylformamide, e.g. dimethylformamide or diethylformamide. The reaction is advantageously accelerated or completed by heating, for example at from 40° to 120° C., preferably from 80° to 100° C. Amongst the solvents, the lower aliphatic ketones, cyclic ethers, dialkylformamides and dimethylsulfoxide are preferred. Mixtures of the said solvents, including mixtures with water, e.g. a dioxane/water mixture, may also be used.

The compounds of the formula III and IV are known or can be prepared by, for example, processes disclosed in the literature, e.g. in Tetrahedron 1967, pages 2,123-2,136, or British Pat. No. 1,269,776. The starting compounds of the formula III may be used in the form of a salt, especially the hydrochloride.

According to a further method of manufacture, the compounds according to the invention, of the general formula (I) are obtained by hydrogenolysis of a compound of the general formula V

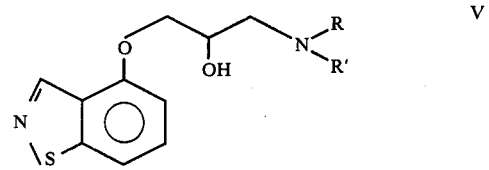

where R has the above meanings and R' is a group removable by hydrogenolysis, or of an addition compound of V with an acid. In the said compounds, R' is advantageously an α-arylalkyl radical, benzyl being especially preferred.

The hydrogenolysis may be carried out as a catalytic hydrogenation, for example in the presence of a transition metal catalyst, preferably a palladium-on-charcoal catalyst, in an inert diluent or solvent, e.g. ethanol or aqueous ethanol, at room temperature or at up to 100° C., but preferably at room temperature, under atmospheric pressure or pressures of up to 200 bars, but preferably under atmospheric pressure. If an amine of the formula V rather than its salt is used, the hydrogenolysis can be accelerated by the presence of an acid, e.g. hydrogen chloride, oxalic acid or maleic acid, as a catalyst.

The starting compounds for the hydrogenolysis process are obtained by the processes described above, using, as the amine component, an amine of the formula HNRR', where R has the above meanings and the particularly preferred meaning of R' is benzyl.

According to yet a further process of manufacture, the compounds of the general formula (I) are obtained by reacting, under reductive amine alkylation conditions, 4-(2-hydroxy-3-amino-propoxy)-1,2-benzisothiazole of the formula VII

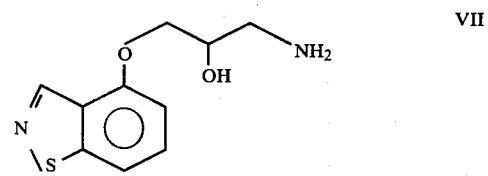

or an addition salt thereof with an acid, and a carbonyl compound of the general formula VIII

where X and Y are hydrogen, alkyl of 1 to 7 carbon atoms, the sum of the carbon atoms of (X+Y) being at most 7 and the alkyl radicals being unsubstituted or substituted as described for R above, or cycloalkyl of 3 to 8 carbon atoms in the ring, or X and Y together with the carbon atom by which they are linked form a bicycloalkyl radical of 5 to 8 carbon atoms, in which the cycloalkyl rings are unsubstituted or substituted by lower alkyl of 1 to 3 carbon atoms.

The reductive amine alkylation is carried out with hydrogen under the conventional reaction conditions for catalytic hydrogenations. Suitable hydrogenation catalysts are transition metals, e.g. palladium, platinum or nickel, preferably palladium on a charcoal carrier, the reaction being carried out in an inert diluent or solvent, e.g. water and/or a lower alcohol of 1 to 4 carbon atoms, e.g. methanol, ethanol or propanol and/or an excess of the carbonyl compound employed as the alkylating agent. The reaction may be carried out under atmospheric pressure or at up to 150 bars, preferably at from 50 to 100 bars, and at room temperature or with heating, for example at from 40° to 120° C.

It should be mentioned that the Schiff's base first formed from the amine of the formula VII and the carbonyl compound can also be reduced by means of an alkali metal borohydride, especially sodium borohydride.

In the course of the reductive amine alkylation, the carbonyl compound of the formula VIII is converted to the radical R, and compounds of the formula I in which the carbon in the α-position to the nitrogen carries at least one hydrogen are obtained. Examples of ketones preferentially used for the reductive amine alkylation are acetone, methoxy acetone, methyl ethyl ketone and methyl propyl ketone.

4-(2-Hydroxy-3-amino-propoxy)-1,2-benzisothiazole of the formula VII is advantageously obtained in accordance with the above processes by reacting a compound of the formula II with ammonia. The reaction of 1-(1,2-benzisothiazol-4-yloxy)-2,3-epoxypropane with aqueous ammonia solution, or the reaction of the same compound, in a solution in an alcohol, preferably ethanol or isopropanol, with gaseous ammonia, are preferred.

The compounds according to the invention, of the formula I, possess a chirality center on carbon atom 2 of the aliphatic side chain and are obtained as racemates, which can be resolved into the optically active antipodes by conventional methods, for example by forming diastereomeric salts with optically active acids, e.g. dibenzoyltartaric acid, camphor-10-sulfonic acid, ditoluyltartaric acid or 3-bromo-camphor-8-sulfonic acid.

The resulting compounds according to the invention may or may not be converted into addition salts with a physiologically safe acid. Examples of suitable conventional physiologically safe organic or inorganic acids are hydrochloric acid, hydrobromic acid, phosphoric acid and sulfuric acid, amongst inorganic acids, and oxalic acid, maleic acid, fumaric acid, lactic acid, tartaric acid, malic acid, citric acid, salicyclic acid, adipic acid and benzoic acid, amongst organic acids; other physiologically safe acids are disclosed in Fortschritte der Arzneimittelforschung, 10 (1966), 224–225, Birkhauser Verlag, Basel and Stuttgart.

The addition salts with acids are as a rule obtained in the conventional manner by mixing the free base or a solution thereof, with the appropriate acid or a solution thereof, in an organic solvent, for example a lower alcohol, e.g. methanol, ethanol or propanol, or a lower ketone, e.g. acetone, methyl ethyl ketone or methyl isobutyl ketone or an ether, e.g. diethyl ether, tetrahydrofuran or dioxane. Mixtures of the said solvents may also be used to improve the deposition of crystals. Furthermore, aqueous solutions, suitable for pharmaceutical use, of acid adducts of the aminopropanol derivatives of the general formula (I) may be prepared by dissolving the free base of the general formula (I) in an aqueous solution of an acid.

The compounds according to the invention, and their physiologically safe addition salts with acids exhibit valuable pharmacological properties and may therefore be used for the treatment and prophylaxis of cardiac and circulatory disorders.

Because of their $\beta$-symphatholytic action, the compounds are particularly suitable for the treatment of coronary cardiac disorders, cardiac arrythmias, and hypertonia.

As shown in the Table which follows, the $\beta$-sympatholytic action was tested on rats, in comparison with the conventional $\beta$-sympatholytic agent Propranolol.

The following methods were used for this purpose:

1. $\beta_1$-sympatholytic action:

Isoproterenol (0.1 μg/kg, given intravenously) in pithed rats (Sprague-Dawley, Mus rattus; weight 230–280 g) causes increases in pulse rate of, on average, 45%. $\beta$-Sympatholytic agents inhibit such tachycardia. Isoproterenol was administered before, and 5 minutes after, the intravenous administration of the test substances. Linear relationships are found between the logarithms of the administered doses (mg/kg) of the test substances and the inhibition (in %) of Isoproterenol tachycardia. From these relationships, the ED 50 values, i.e. the doses which inhibit the Isoproterenol tachycardia by 50%, are determined.

2. $\beta_2$-sympatholytic action:

The inhibition, by $\beta$-sympatholytic agents, of the reduction in blood pressure induced by Isoproterenol was tested on rats, weighing 230–280 g, under urethane narcosis (1.78 g of urethane/kg being administered intraperitoneally). Isoproterenol (0.215 μg/kg given intravenously) reduces the mean pressure of the carotid artery by an average of 30%. $\beta$-Sympatholytic agents inhibit this action.

Linear relationships exist between the logarithms of the doses used and the inhibition of the Isoproterenol blood pressure reduction, from which the ED 50 values, i.e. the doses which inhibit the Isoproterenol blood pressure reduction by 50%, were determined.

3. Acute toxicity:

The acute toxicity was determined on groups of 10 or 20 female Swiss mice weighing 20–26 g, the compounds being administered intraperitoneally. The LD 50 was taken to be the calculated dose (Probit analysis) after which 50% of the animals died within 24 hours.

Table 1 shows that the pharmacotherapeutically important $\beta$-1-sympatholytic activity of the compounds of the invention is from 2.5 times (Example 29) to 8 times (Example 14) greater than that of the comparative substance Propranolol. In addition, the substances exhibit a greater cardioselectivity than Propranolol, i.e. the pharmacotherapeutically desirable effect on cardiac $\beta_1$-receptors manifests itself at lower doses than the effect of the $\beta_2$-receptors on the blood vessels. In the case of Propranolol, about equal doses are required for both these inhibiting effects. The test substances block cardiac $\beta_1$-receptors at doses which are from 2 times (Example 1) to 11 times (Example 35) lower than those required to block $\beta_2$-receptors.

The therapeutic range, expressed as the quotient of the 50% lethal dose (LD 50) and the 50% $\beta_1$-blocking dose (ED 50) is from 3 times (Example 35) to 11 times (Example 2) greater than for Propranolol.

TABLE 1

| | β-Sympatholytic action and acute toxicity | | | | | | | |
|---|---|---|---|---|---|---|---|---|
| | $\beta_1$-Sympatholytic action 1 | | $\beta_2$-Sympatholytic action 4 | | | Acute toxicity | Thera- peutic range 8 | |
| Example No. | ED 50 2 | R.A. 3 | ED 50 5 | R.A. 3 | Q 6 | LD 50 7 | absolute | relative 9 |
| 1 | 0.00190 | 6.47 | 0.00420 | 2.71 | 2.21 | 62.1 | 32,700 | 3.72 |
| 2 | 0.00163 | 7.55 | 0.00402 | 2.84 | 2.47 | 154 | 94,500 | 10.76 |
| 14 | 0.00153 | 8.04 | 0.0106 | 1.08 | 6.93 | 96.4 | 63,000 | 7.18 |
| 15 | 0.00184 | 6.68 | 0.00824 | 1.38 | 4.48 | 144 | 78,300 | 8.92 |
| 16 | 0.00328 | 3.75 | 0.0121 | 0.94 | 3.69 | 128 | 39,000 | 4.44 |
| 27 | 0.00230 | 5.35 | 0.00575 | 1.98 | 2.50 | 184 | 80,000 | 9.11 |
| 29 | 0.00495 | 2.48 | 0.0440 | 0.26 | 8.90 | 135 | 27,300 | 3.11 |
| 35 | 0.00252 | 4.88 | 0.0270 | 0.42 | 10.70 | 60.3 | 23,900 | 2.72 |
| Propranolol | 0.0123 | 1.00 | 0.0114 | 1.00 | 0.93 | 108 | 8,780 | 1.00 |

1 Inhibition of Isoproterenol tachycardia (IT). Pithed rats. Intravenous administration
2 Dose (mg/kg) which inhibits the IT by 50%
3 Relative activity. Propranolol = 1.00
4 Inhibition of Isoproterenol blood pressure reduction (IBP). Rats under urethane narcosis. Intravenous administration.
5 Dose (mg/kg) which inhibits the IBP by 50%
6 $Q = \dfrac{\text{ED 50 for } \beta_2\text{-sympatholysis}}{\text{ED 50 for } \beta_1\text{-sympatholysis}}$
7 Mice, intraperitoneal administration
8 $\dfrac{\text{LD 50}}{\text{ED 50 (IT)}}$
9 Propranolol = 1.00

Accordingly, the present invention also relates to therapeutic agents or formulations which contain a compound of the formula I as the active ingredient, together with conventional excipients and diluents, and to the use of the new compounds for therapeutic purposes.

The agents or formulations are prepared in the conventional manner by compounding an appropriate dose with the conventional excipients or diluents and the conventional pharmaceutical auxiliaries, in accordance with the desired route of administration.

The preferred formulations are those suitable for oral administration. Examples of these are tablets, film tablets, dragees, capsules, pills, powders, solutions or suspensions, or forms which exert a depot effect.

Of course, formulations for parenteral administration, e.g. injection solutions, are also suitable. Suppositories are a further example of suitable formulations.

Appropriate tablets can be obtained, for example, by mixing the active ingredient with conventional auxiliaries, for example inert excipients, e.g. dextrose, sugar, sorbitol, mannitol, polyvinylpyrrolidone, calcium carbonate, calcium phosphate or lactose, disintegrating agents, e.g. corn starch, or alginic acid, binders, e.g. starch or gelatin, lubricants, e.g. magnesium stearate or talc, and/or agents added in order to achieve a depot effect, e.g. carboxypolymethylene, carboxymethylcellulose, cellulose acetate-phthalate or polyvinyl acetate. The tablets may also consist of a plurality of layers.

Dragees may be produced by coating cores, prepared similarly to the tablets, with agents conventionally used in dragee coatings, for example polyvinylpyrrolidone or shellac, gum arabic, talc, titanium dioxide or sugar. The dragee coating may also consist of a plurality of layers, and the auxiliaries referred to above in connection with tablets may be employed.

Solutions or suspensions containing the active ingredients according to the invention may in addition contain agents for improving the taste, e.g. saccharin, cyclamate or sugar, as well as, for example, flavorings, e.g. vanillin or orange extract. Furthermore, they may contain dispersants, e.g. sodium carboxymethylcellulose, or preservatives, e.g. p-hydroxybenzoates. Capsules containing the active ingredient may be produced, for example, by mixing the active ingredient with an inert carrier, e.g. lactose or sorbitol, and encapsulating the mixture in gelatin capsules.

Suitable suppositories may be produced, for example, by mixing the active ingredient with an appropriate carrier for suppositories, e.g. a neutral fat or polyethylene glycol or a derivative thereof.

For man, a suitable single dose of the compounds according to the invention is from 1 to 100 mg, preferably from 3 to 50 mg.

The following compounds are singled out because of their activity: 4-(2-hydroxy-3-isopropylamino-propoxy)-1,2-benzisothiazole, 4-(2-hydroxy-3-tert.-butylamino-propoxy)-1,2-benzisothiazole, 4-[2-hydroxy-3-(3-methyl-pentyl-3-amino)-propoxy]-1,2-benzisothiazole, 4-[2-hydroxy-3-(2-methyl-butyl-2-amino)-propoxy]-1,2-benzisothiazole, 4-[2-hydroxy-3-(2-methyl-but-3-ynyl-2-amino)-propoxy]-1,2-benzisothiazole and 4-(2-hydroxy-3-sec.-butylamino-propoxy)-1,2-benzisothiazole, 4-[2-hydroxy-3-(1-methoxy-propyl-2-amino)-propoxy]-1,2-benzisothiazole and 4-[2-hydroxy-3-(pentyl-2-amino)-propoxy]-1,2-benzisothiazole.

The Examples which follow illustrate the invention.
Preparation of starting compounds

EXAMPLE I 50 g of 4-methoxy-1,2-benzisothiazole are suspended in 700 ml of acetic acid containing 10% by weight of hydrogen bromide and 5 g of red phosphorus, and the suspension is heated for 30 hours at 100° C. in a tantalum autoclave. After cooling, the material discharged from the autoclave is concentrated under reduced pressure and the residue is partitioned between methylene chloride and 2 N sodium hydroxide solution. The water phase is filtered to remove insoluble matter, washed with methylene chloride, acidified with hydrochloric acid and then repeatedly extracted with methylene chloride. The combined extracts are dried over magnesium sulfate and then concentrated under reduced pressure. 32 g (65% of theory) of 4-hydroxy-1,2-benzisothiazole of melting point 133°–134° C. are obtained. $C_7H_5ONS$ (151)

calculated:  55.6 C   3.3 H   10.6 O   9.3 N   21.2 S

| | | | | | | | | | |
|---|---|---|---|---|---|---|---|---|---|
| found: | 56.1 | C | 3.4 | H | 10.5 | O | 9.1 | N | 20.8 S |

If the methylene chloride phases which have been washed with 2-normal sodium hydroxide solution are worked up in the conventional manner, 20–25% of the 4-methoxy-1,2-benzisothiazole employed can be recovered and recycled to a subsequent ether cleavage.

EXAMPLE II 1-(1,2-Benzisothiazol-4-yloxy)-2,3-epoxy-propane 29 g of 4-hydroxy-1,2-benzisothiazole, 36 g of epibromohydrin and 93 g of dry potassium carbonate in 300 ml of acetone are refluxed for 11 hours. When it has cooled, the entire reaction mixture is poured into 1 liter of ice water and extracted with four times 150 ml of diethyl ether, and the combined extracts are washed with water and dried over sodium sulfate. After distilling off the solvent, 30 g (75% of theory) of 1-(1,2-benzisothiazol-4-yloxy)-2,3-epoxy-propane of melting point 85°–87° C. remain and can be used further without purification.

Analytically pure 1-(1,2-benzisothiazol-4-yloxy)-2,3-epoxy-propane of melting point 90°–91° C. is obtained by sublimation at 110°–130° C. under 0.2 mm Hg. $C_{10}H_9O_2NS$ (207)

| | | | | | | | | | |
|---|---|---|---|---|---|---|---|---|---|
| calculated | 58.0 | C | 4.4 | H | 15.4 | O | 6.8 | N | 15.5 S |
| found | 57.7 | C | 4.6 | H | 15.4 | O | 6.8 | N | 15.1 S |

EXAMPLE III 4-(2-Hydroxy-3-aminopropoxy)-1,2-benzisothiazole 4.0 g of 1-(1,2-benzisothiazol-4-yloxy)-2,3-epoxy-propane in 100 ml of aqueous ammonia and 300 ml of ethanol are left to stand for 3 hours at 35° C. The mixture is concentrated, the semi-crystalline residue is dissolved in ethanol and a solution of hydrogen chloride in ether is added dropwise. The hydrochloride which precipitates is filtered off, washed with dry ether and dried.

Yield: 3.1 g (60% of theory), melting point 240°–243° C. $C_{10}H_{13}O_2N_2SCl$ (261)

| | | | | | | | | | | | |
|---|---|---|---|---|---|---|---|---|---|---|---|
| calculated | 46.1 C | 5.0 H | 12.3 O | 10.7 N | 12.3 S | 13.6 Cl |
| found | 45.3 C | 5.0 H | 12.9 O | 10.3 N | 11.7 S | 13.9 Cl |

EXAMPLE IV

4-[2-Hydroxy-3-(N-benzyl-isopropylamino)-propoxy]-1,2-benzisothiazole 2.0 g of 1-(1,2-benzisothiazol-4-yloxy)-2,3-epoxy-propane and 1.5 g of N-benzylisopropylamine in 50 ml of ethanol are refluxed for 2 hours. The 4-[2-hydroxy-3-(N-benzylisopropylamino)-propoxy]-1,2-benzisothiazole which is left after distilling off the solvent may be used directly, in the form obtained, for debenzylation. To characterize the compound, it is dissolved in a little methanol and a solution of oxalic acid in ether is added dropwise. The 4-[2-hydroxy-3-(N-benzylisopropylamino)-propoxy]-1,2-benzisothiazole hydrogen oxalate which precipitates is filtered off, washed with dry ether and dried. Melting point 176°–178° C. $C_{22}H_{26}N_2O_6S$ (446)

| | | | | | | | | | |
|---|---|---|---|---|---|---|---|---|---|
| calculated | 59.2 | C | 5.8 | H | 6.3 | N | 21.5 | O | 7.2 S |
| found | 58.9 | C | 5.7 | H | 6.2 | N | 21.3 | O | 7.3 S |

EXAMPLE V 1-(1,2-Benzisothiazol-4-yloxy)-3-chloro-propan-2-ol (a) 2.0 g of 1-(1,2-benzisothiazol-4-yloxy)-2,3-epoxy-propane are suspended in a mixture of 30 ml of ethanol and 30 ml of diethyl ether and 100 ml of a solution of hydrogen chloride in ether are added whilst stirring. After standing for three days the precipitate formed is filtered off and washed neutral with ether.

Yield: 2.2 g (91% of theory) of melting point 90°–92° C.

1-(1,2-Benzisothiazol-4-yloxy)-3-chloro-propan-2-ol which is pure according to NMR spectroscopy and has a melting point of 104°–106° C. is obtained by recrystallization from methanol.

$^1$H-NMR spectrum ($d_6$-DMSO, TMS as internal standard): $\tau = 0.82$ (s, 1H), 2.22 (d, J=4.5 Hz, 1H), 2.42 (m, 1H), 2.99 (d, J=3.0 Hz, 1H), 3.62 (s, 0H), 5.73 (m, 3H), 6.11 (m, 2H).

(b) 15.0 g of 4-hydroxy-1,2-benzisothiazole and 100 mg of 2,2,6,6-tetramethylpiperidine are heated with 30 ml of epichlorohydrin for 6 hours at 100°–110° C. The mixture is then freed from excess epichlorohydrin under reduced pressure and the residue is digested with three times 100 ml of methanol. The combined methanol extracts are evaporated to dryness under reduced pressure. 10.4 g of a semi-crystalline residue remain; the $^1$H-NMR spectrum of this material agrees with that of 1-(1,2-benzisothiazol-4-yloxy)-3-chloropropan-2-ol from (a).

(c) 30.0 g of 4-hydroxy-1,2-benzisothiazole are suspended in 26.0 g of 1,3-dichloro-propan-2-ol and a solution of 8.5 g of sodium hydroxide in 60 ml of water is added in the course of 4 hours at 60°–80° C. After reacting for a further four hours at the same temperature, the organic phase is taken up in methylene chloride, dried over magnesium sulfate and evaporated to dryness. The residue left (35 g) is recrystallized from methanol. The 1-(1,2-benzisothiazol-4-yloxy)-3-chloropropan-2-ol thus obtained is identical with the sample prepared as described in (a). Preparation of compounds according to the invention

EXAMPLE 1

50 g of 1-(1,2-benzisothiazol-4-yloxy)-2,3-epoxy-propane and 25 ml of isopropylamine in 50 ml of ethanol are refluxed for 2 hours. The residue which is left after distilling off the solvent and excess amine is dissolved in 5 ml of ethanol and a solution of hydrogen chloride in ether is added dropwise. The 4-(2-hydroxy-3-isopropylaminopropoxy)-1,2-benzisothiazole hydrochloride which precipitates is filtered off, washed with dry ether and dried.

Yield: 6.0 g (83% of theory) of melting point 158°–160° C. $C_{13}H_{19}O_2N_2SCl$ (303)

| | | | | | | |
|---|---|---|---|---|---|---|
| calculated | 51.6 C | 6.3 H | 10.6 O | 9.3 N | 10.6 S | 11.7 Cl |
| found | 51.4 C | 6.5 H | 11.4 O | 9.4 N | 10.2 S | 11.5 Cl |

EXAMPLE 2

Using the method described in Example 1, 50 g of 1-(1,2-benzisothiazol-4-yloxy)-2,3-epoxy-propane and 25 ml of tert.-butylamine give 6.3 g (80% of theory) of 4-(2-hydroxy-3-tert.-butylamino-propoxy)-1,2-benzisothiazole hydrochloride of melting point 190°–192° C. $C_{14}H_{21}O_2N_2SCl$ (317)

| | | | | | | | | | | |
|---|---|---|---|---|---|---|---|---|---|---|
| calculated | 53.1 | C | 6.7 | H | 10.1 | O | 8.8 | N | 10.1 S | 11.2 Cl |
| found | 52.7 | C | 6.5 | H | 10.5 | O | 8.7 | N | 10.0 S | 11.3 Cl |

EXAMPLE 3

50 g of 1-(1,2-benzisothiazol-4-yloxy)-2,3-epoxy-propane are reacted with tert.-butylamine as described in Example 1 and the product is then converted by treatment with a solution of maleic acid in ether into 4-(2-hydroxy-3-tert.-butylaminopropoxy)-1,2-benzisothiazole hydrogen maleate.

Yield: 5.4 g (55% of theory) of melting point 158°–161° C. $C_{18}H_{24}O_6N_2S$ (396)

| | | | | | | | | | |
|---|---|---|---|---|---|---|---|---|---|
| calculated | 54.5 | C | 6.1 | H | 24.2 | O | 7.1 | N | 8.1 S |
| found | 54.0 | C | 6.2 | H | 24.6 | O | 6.7 | N | 7.9 S |

EXAMPLE 4

Using the same method, 5.1 g (55% of theory) of 4-(2-hydroxy-3-tert.-butylamino-propoxy)-1,2-benzisothiazole hydrogen oxalate, of melting point 158°–160° C., are obtained as described in Example 1. $C_{16}H_{22}O_6N_2S$ (370)

| | | | | | | | | | |
|---|---|---|---|---|---|---|---|---|---|
| calculated | 51.9 | C | 6.0 | H | 25.9 | O | 7.6 | N | 8.7 S |
| found | 51.5 | C | 6.0 | H | 25.9 | O | 7.4 | N | 8.3 S |

EXAMPLE 5

3.6 g of 4-[2-hydroxy-3-(N-benzylisopropylamino)-propoxy]-1,2-benzisothiazole are dissolved in 100 ml of ethanol and the solution is shaken with 0.7 g of a 5% strength palladium-on-charcoal catalyst under a hydrogen atmosphere, until saturation is reached. After filtering off the catalyst, the ethanol, and the toluene formed, are distilled off under reduced pressure, the residue is suspended in 100 ml of 10% strength aqueous hydrochloric acid and the suspension is washed three times with ether. The aqueous phase is rendered alkaline with 5 N sodium hydroxide solution whilst cooling with ice and is extracted with four times 100 ml of ether. These extracts are dried by means of sodium sulfate and evaporated, and the residue is converted, by the method described in Example 1, into 4-(2-hydroxy-3-isopropylamino-propoxy)-1,2-benzisothiazole hydrochloride. Yield 1.8 g (60% of theory), melting point 156°–160° C.

EXAMPLE 6

2.4 g of 1-(1,2-benzisothiazol-4-yloxy)-3-chloropropan-2-ol and 10 ml of (1,2-dimethylpropyl)-amine in 50 ml of dioxane are heated for 10 hours in an autoclave at 100° C. After distilling off the volatile constituents under reduced pressure, the highly viscous crude product is partitioned between ether and 4 N sulfuric acid, and the aqueous phase is cautiously rendered alkaline with 4 N sodium hydroxide solution and is finally extracted with ether. After drying the organic phase over sodium sulfate, the solvent is removed and the residue left is converted to 4-[2-hydroxy-3-(3-methylbutyl-2-amine)-propoxy]-1,2-benzisothiazole hydrochloride by the method described in Example 1.

Yield: 1.8 g (54% of theory), melting point 161°–164° C. $C_{15}H_{20}N_2O_2SCl$ (331)

| | | | | | | | | | | |
|---|---|---|---|---|---|---|---|---|---|---|
| calculated | 54.5 | C | 7.0 | H | 9.7 | O | 8.5 | N | 9.7 S | 10.7 Cl |
| found | 54.0 | C | 6.8 | H | 10.5 | O | 8.2 | N | 9.4 S | 10.7 Cl |

EXAMPLE 7

Using isopropylamine and 1-(1,2-benzisothiazol-4-yloxy)-3-chloro-propan-2-ol as the starting materials, 4-(2-hydroxy-3-isopropylamino-propoxy)-1,2-benzisothiazole hydrochloride is obtained by the method described in Example 6. The compound is identical with that obtained as described in Example 1.

Using the same method, tert.-butylamine gives 4-(2-hydroxy-3-tert.-butylamino-propoxy)-1,2-benzisothiazole hydrochloride, which is identical with the compound from Example 2.

EXAMPLE 8

3.0 g of 4-hydroxy-1,2-benzisothiazole and 5.0 g of 1-chloro-3-isopropylaminopropan-2-ol hydrochloride in 100 ml of a water-dioxane mixture (20:80 by volume) are refluxed with 2 g of sodium hydroxide for 10 hours. When the mixture has cooled, it is extracted with five times 100 ml of chloroform and the combined extracts are washed with water, dried over sodium sulfate and evaporated to dryness. A part of the residue left is chromatographed on a dry silica gel column, using a methanol-methylene chloride mixture (60:40 by volume). The very viscous, pale yellow residue left on evaporating the eluate is converted to 4-(2-hydroxy-3-isopropylamino-propoxy)-1,2-benzisothiazole hydrochloride by the method described in Example 1. The substance is identical with the compound obtained as described in Example 1.

In the same way, tert.-butylamine gives 4-(2-hydroxy-3-tert.-butylamino-propoxy)-1,2-benzisothiazole hydrochloride, which is identical with the compound from Example 2.

EXAMPLE 9

4.4 g of 4-(2-hydroxy-3-amino-propoxy)-1,2-benzisothiazole and 0.1 g of a 10% strength palladium-on-charcoal catalyst, in a mixture of 50 ml of methanol and 100 ml of acetone, are left for 24 hours at 60° C. under 100 bars hydrogen pressure. The mixture is freed from catalyst by filtration, and is concentrated. The residue left is converted to 4-(2-hydroxy-3-isopropylamino-propoxy)-1,2-benzisothiazole hydrochloride by the method described in Example 1. The substance is identical with the compound obtained as described in Example 1.

The compounds shown in the Table which follows are obtained from 1-(1,2-benzisothiazol-4-yloxy)-2,3-epoxy-propane and the corresponding amines, by the method described in Example 1.

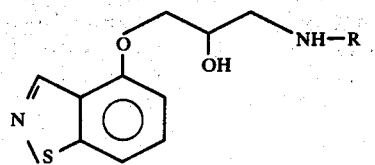

| Ex. No. | —R | Salt with acid | Melting point °C. | |
|---|---|---|---|---|
| 10 | —CH(CH₃)CH₂—N(piperidino) | HOOC—COOH | 95–97 | 4-[2-Hydroxy-3-(3-piperidino-propyl-2-amino)-propoxy]-1,2-benzisothiazole |
| 11 | —CH₃ | HCl | 186–190 | 4-(2-Hydroxy-3-methylamino-propoxy)-1,2-benzisothiazole |
| 12 | -nC₄H₉ | HCl | 163–165 | 4-(2-Hydroxy-3-butylamino-propoxy)-benzisothiazole |
| 13 | —CH₂—CH(CH₃)₂ | — | 94–97 | 4-(2-Hydroxy-3-isobutylamino-propoxy)-1,2-benzisothiazole |
| 14 | —CH(CH₃)C₂H₅ | COOH-COOH | 146–148 | 4-(2-Hydroxy-3-sec.-butylamino-propoxy)-1,2-benzisothiazole |
| 15 | —C(CH₃)₂—CH₂—CH₃ | HCl | 182–184 | 4-[2-Hydroxy-3-(2-methyl-butyl-2-amino)-propoxy]-1,2-benzisothiazole |
| 16 | —C(C₂H₅)₂—CH₃ | HCl | 180–182 | 4-[2-Hydroxy-3-(3-methyl-pentyl-3-amino)-propoxy]-1,2-benzisothiazole |
| 17 | —C(CH₃)₂—CH(CH₃)₂ | HCl | 214–216 | 4-[2-Hydroxy-3-(2,3-dimethyl-butyl-2-amino)-propoxy]-1,2-benzisothiazole |
| 18 | —C(C₂H₅)₃ | — | 125 | 4-[2-Hydroxy-3-(3-ethyl-pentyl-3-amino)-propoxy]-1,2-benzisothiazole |
| 19 | —CH[CH(CH₃)₂]₂ | HCl | 175–178 | 4-[2-Hydroxy-3-(2,4-dimethyl-pentyl-3-amino)-propoxy]-1,2-benzisothiazole |
| 20 | cyclopropyl | HCl | 186–190 | 4-(2-Hydroxy-3-cyclopropylamino-propoxy)-1,2-benzisothiazole |
| 21 | cyclopentyl | COOH-COOH | 168–170 | 4-(2-Hydroxy-3-cyclopentylamino-propoxy)-1,2-benzisothiazole |
| 22 | cycloheptyl | HCl | 160–162 | 4-(2-Hydroxy-3-cycloheptylamino-propoxy)-1,2-benzisothiazole |
| 23 | bicyclo[3.3.0]octyl | HCl | 201–203 | 4-[2-Hydroxy-3-(bicyclo[3.3.0]octyl-1-amino)-propoxy]-1,2-benzisothiazole |
| 24 | 2-norbornanyl | COOH-COOH | 202–203 | 4-[2-Hydroxy-3-(2-exo-norbornanylamino)-propoxy]-1,2-benzisothiazole |
| 25 | —C(CH₃)₂—CH₂—C(CH₃)₃ | COOH-COOH | 161–163 | 4-[2-Hydroxy-3-(2,4,4-trimethyl-pentyl-2-amino)-propoxy]-1,2-benzisothiazole |
| 26 | —C(CH₃)₂—CH₂—S—CH₃ | COOH-COOH | 154–156 | 4-[2-Hydroxy-3-(1-thiomethyl-2-methyl-propyl-2-amino)-propoxy]-1,2-benzisothiazole |

-continued

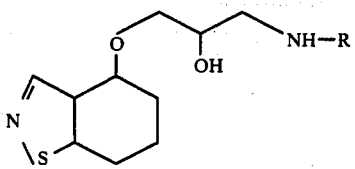

| Ex. No. | —R | Salt with acid | Melting point °C. | |
|---|---|---|---|---|
| 27 | CH₃ \| —C—C≡CH \| CH₃ | HCl | 151–153 | 4-[2-Hydroxy-3-(2-methyl-but-3-ynyl-2-amino)-propoxy]-1,2-benzisothiazole |
| 28 | —CH(CH₃)(C≡CH) | HCl | 178–181 | 4-[2-Hydroxy-3-(but-3-ynyl-2-amino)-propoxy]-1,2-benzisothiazole |
| 29 | —CH(CH₂OCH₃)(CH₃) | COOH \| COOH | 152–156 | 4-[2-Hydroxy-3-(1-methoxy-propyl-2-amino)-propoxy]-1,2-benzisothiazole |
| 30 | —CH(CH₃)(CH₃) | COOH \| COOH | 159–161 | 4-[2-Hydroxy-3-isopropylamino-propoxy]-1,2-benzisothiazole |
| 31 | cyclooctenyl | COOH \| COOH | 179–183 | 4-[2-Hydroxy-3-(cyclooctenyl-4-amino)-propoxy]-1,2-benzisothiazole |
| 32 | 2,6-dimethylcyclohexyl | HCl | 193–197 | 4-[2-Hydroxy-3-(2,6-dimethyl-cyclohexyl-1-amino)-propoxy]-1,2-benzisothiazole |
| 33 | C₂H₅ \| —C—C≡CH \| C₂H₅ | HCl | 177–179 | 4-[2-Hydroxy-3-(3-ethyl-pent-1-ynyl-3-amino)-propoxy]-1,2-benzisothiazole |
| 34 | —CH₂—CH=CH₂ | — | 83–85 | 4-[2-Hydroxy-3-(prop-1-ynyl-3-amino)-propoxy]-1,2-benzisothiazole |
| 35 | —CH(CH₃)(CH₂—CH₂—CH₃) | HOOC—COOH | 154–156 | 4-[2-Hydroxy-3-(pentyl-2-amino)-propoxy]-1,2-benzisothiazole |
| 36 | —CH(CH₃)(cyclopropyl) | HOOC—COOH | 162–164 | 4-[2-Hydroxy-3-(1-cyclopropyl-ethyl-1-amino)-propoxy]-1,2-isothiazole |
| 37 | —CH₂—CH₂—OH | HCl | 131–133 | 4-[2-Hydroxy-3-(2-hydroxy-ethylamino)-propoxy]-1,2-benzisothiazole |
| 38 | —CH(CH₂OH)(CH₂—CH₃) | HOOC—COOH | 136–138 | 4-[2-Hydroxy-3-(1-hydroxy-butyl-2-amino)-propoxy]-1,2-benzisothiazole |
| 39 | —CH₂—CH₂—C(CH₃)(OH)(CH₃) | HOOC—COOH | 182–184 | 4-[2-Hydroxy-3-(3-hydroxy-3-methyl-butyl-2-amino)-propoxy]-1,2-benzisothiazole |

EXAMPLES 40 to 70

The compounds shown in the preceding Table are obtained equally if 1-(1,2-benzisothiazol-4-yloxy)-3-chloro-propan-2-ol is reacted with the corresponding amines by the method described in Example 6.

There follow examples of formulations which are prepared in the conventional manner.

| 1. | Tablets | |
|---|---|---|
| (a) | An active ingredient of the formula I | 5 mg |
| | lactose | 200 mg |
| | methylcellulose | 15 mg |
| | corn starch | 50 mg |
| | talc | 11 mg |

-continued

| 1. | Tablets | |
|---|---|---|
| | magnesium stearate | 4 mg |
| | | 285 mg |
| (b) | An active ingredient of the formula I | 20 mg |
| | lactose | 178 mg |
| | Avicel | 80 mg |
| | Polywax 6000 | 20 mg |
| | magnesium stearate | 2 mg |
| | | 300 mg |
| (c) | An active ingredient of the formula I | 50 mg |
| | polyvinylpyrrolidone (mean molecular weight 25,000) | 170 mg |
| | polyethylene glycol (mean molecular weight 4,000) | 14 mg |
| | hydroxypropylmethylcellulose | 40 mg |
| | talc | 4 mg |

| 1. | Tablets | |
|---|---|---|
| | magnesium stearate | 2 mg |
| | | 280 mg |

The active ingredient is moistened with a 10% strength aqueous solution of polyvinylpyrrolidone and the mixture is forced through a sieve of 1.0 mm mesh width and dried at 50° C. These granules are mixed with the polyethylene glycol (of mean molecular weight 4,000), hydroxypropylmethylcellulose, talc and magnesium stearate, and the mixture is molded into tablets each weighing 280 mg.

| 2. | Dragees | |
|---|---|---|
| | Compound of the formula I | 3 mg |
| | lactose | 90 mg |
| | corn starch | 60 mg |
| | polyvinylpyrrolidone | 6 mg |
| | magnesium stearate | 1 mg |
| | | 160 mg |

The mixture of the active ingredient with the lactose and corn starch is granulated by compounding with an 8% strength aqueous solution of the polyvinylpyrrolidone and forcing through a 1.5 mm sieve; the granules are dried at 50° C. and forced through a 1.0 mm sieve. The granules thus obtained are mixed with the magnesium stearate and molded into dragee cores. The latter are provided with a coating, consisting essentially of sugar and talc, in the conventional manner.

| 2. | Capsules | |
|---|---|---|
| | Compound of the formula I | 5.0 mg |
| | magnesium stearate | 2.0 mg |
| | lactose | 19.3 mg |
| 4. | Injection solution | |
| | Compound of the formula I | 10 mg |
| | sodium chloride | 9 mg |
| | distilled water to make up to 1.0 ml | |

We claim:

1. A compound of the formula I

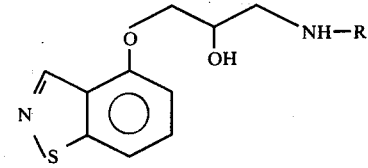

where R is alkyl of 3 to 6 carbon atoms, which is branched at the carbon in the α-position to the nitrogen, and is unsubstituted or substituted by one alkoxy of 1 to 3 carbon atoms, or is 2-methyl-but-3-ynyl-2, and addition salts of said compound with physiologically safe acids.

2. 4-(2-Hydroxy-3-isopropylamino-propoxy)-1,2-benzisothiazole.

3. 4-(2-Hydroxy-3-tert.-butylamino-propoxy)-1,2-benzisothiazole.

4. 4-(2-Hydroxy-3-sec.-butylamino-propoxy)-1,2-benzisothiazole.

5. 4-[2-Hydroxy-3-(2-methyl-butyl-2-amino)-propoxy]-1,2-benzisothiazole.

6. 4-[2-Hydroxy-3-(2-methyl-but-3-ynyl-2-amino)-propoxy]-1,2-benzisothiazole.

7. A pharmaceutical composition for use in the treatment of cardiac disease consisting essentially of an active ingredient of a compound of the formula

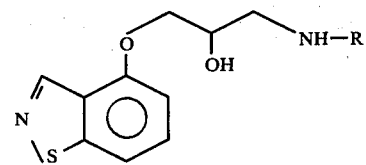

where R is alkyl of 3 to 6 carbon atoms, which is branched at the carbon in the α-position to the nitrogen, and is unsubstituted or substituted by one alkoxy of 1 to 3 carbon atoms, or is 2-methyl-but-3-ynyl-2 and the pharmaceutically acceptable non-toxic acid addition salts thereof, and a pharmaceutically acceptable carrier.

8. A pharmaceutical composition as set forth in claim 7 wherein the compound is 4-(2-hydroxy-3-isopropylamino-propoxy)-1,2-benzisothiazole or one of its addition salts.

9. A pharmaceutical composition as set forth in claim 7 wherein the compound is 4-(2-hydroxy-3-tert.-butylamino-propoxy)-1,2-benzisothiazole or one of its addition salts.

10. A pharmaceutical composition as set forth in claim 7 in dosage form which contains from 1 to 100 mg.

* * * * *